(12) United States Patent
Kaspi et al.

(10) Patent No.: US 6,570,044 B2
(45) Date of Patent: May 27, 2003

(54) PROCESS FOR THE PREPARATION OF 6,6-DIMETHYLHEPT-1-EN-4-YN-3-OL

(75) Inventors: Joseph Kaspi, Givatayim (IL); Oded Friedman, Holon (IL); Edna Danon, Meitar (IL)

(73) Assignee: Chemagis Ltd., Tel Aviv (IL)

( * ) Notice: Subject to any disclaimer, the term of this patent is extended or adjusted under 35 U.S.C. 154(b) by 0 days.

(21) Appl. No.: 09/906,105

(22) Filed: Jul. 17, 2001

(65) Prior Publication Data
US 2002/0016517 A1 Feb. 7, 2002

(30) Foreign Application Priority Data
Jul. 18, 2000 (IL) .................................................. 137364

(51) Int. Cl.⁷ .............................................. C07C 33/04
(52) U.S. Cl. ...................................................... 568/874
(58) Field of Search .......................................... 568/874

(56) References Cited

U.S. PATENT DOCUMENTS

| 2,783,258 A | * | 2/1957 | Celmer |
| 4,382,951 A | * | 5/1983 | Grassberger |
| 4,755,534 A | * | 7/1988 | Stuetz |
| 5,036,158 A | * | 7/1991 | Meki |

* cited by examiner

Primary Examiner—Michael L. Shippen
(74) Attorney, Agent, or Firm—Banner & Witcoff, Ltd.

(57) ABSTRACT

The invention provides a process for the preparation of 6,6-dimethylhept-1-en-4-yn-3-ol comprising of reacting t-butylacetylene with a proton-extracting agent selected from the group consisting of an organometallic compound and metallic lithium to form a t-butylacetylide, reacting the acetylide with acrolein at temperatures between −40° C. to +20° C., quenching the reaction mixture and isolating the product.

4 Claims, No Drawings

PROCESS FOR THE PREPARATION OF 6,6-DIMETHYLHEPT-1-EN-4-YN-3-OL

FIELD OF THE INVENTION

The present invention relates to a technologically improved chemical process for the preparation of 6,6-dimethylhept-1-en-4-yn-3-ol. This compound is an important intermediate for the production of the widely used antifungal drug terbinafine.

PRIOR ART

The synthesis of the antifungal drug terbinafine was described in the chemical literature using various synthetic routes. Out of the processes described in the literature two closely related synthetic routes emerge as very significant processes for the preparation of terbinafine.

European patent EP24,587 describes the following process:

Reacting t-butylacetylene at −20° C. with butyllithium, cooling the reaction mixture to −75° C. and reacting it with acrolein to give 6,6-dimethylhept-1-en-4-yn-3-ol.

Treating the 6,6-dimethylhept-1-en-4-yn-3-ol formed with phosphorous tribromide in hydrobromic acid to give a mixture of Z and E isomers of 1-bromo-6,6-dimethylhept-2-en-4-yne. Usually the isomer ratio obtained is Z:E~1:2 to 1:3.

Treating the bromo compound (isomer mixture) with N-methyl-N-(1-naphthylmethyl)amine to give terbinafine.

The process is given in scheme 1.

SCHEME 1

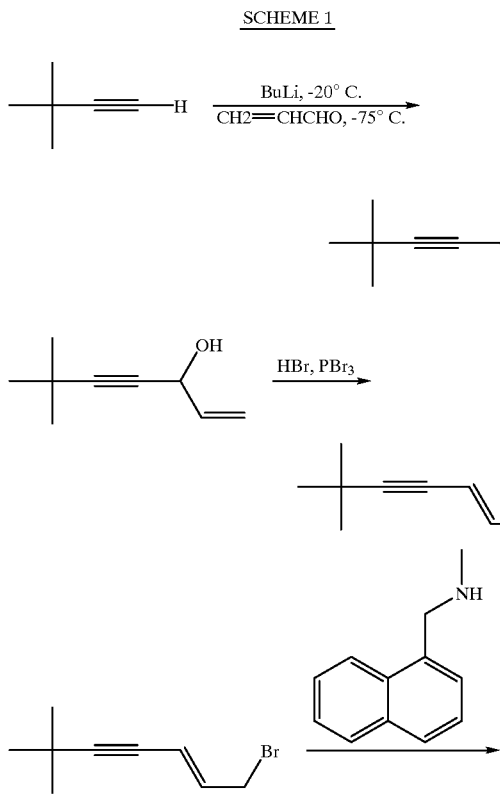

The second process is described in Spanish Patent ES550,015 that uses similar building blocks. The process is as follows:

Reacting 1-bromo-6,6-dimethylhept-2-en-4-yne with excess methylamine to form N-methyl-N-(6,6-dimethylhept-2-en-4-ynyl)amine.

Reacting the said amine with 1-chloromethylnaphthalene to form terbinafine

This process is described in scheme 2.

SCHEME 2

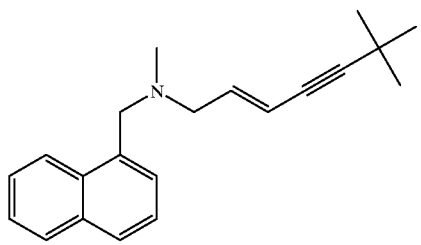

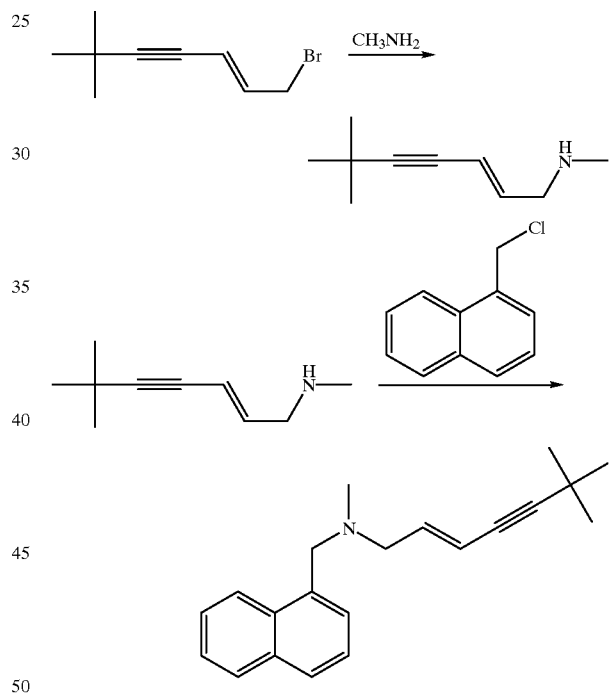

The second process uses the same precursor, namely 6,6-dimethylhept-1-en-4-yn-3-ol, to prepare the required bromo compound.

The synthesis of the chloro analog viz. 1-chloro-6,6-dimethylhept-2-en-4-yne is described in European Patent EP341,048. In this patent the following synthesis is described:

Reacting t-butylacetylene at −40° C. or less with butyllithium, cooling the reaction mixture at −40° C. or less with acrolein further aging the reaction mixture at −50° C. for 30 minutes to give 6,6-dimethylhept-1-en-4-yn-3-ol.

Treating the 6,6-dimethylhept-1-en-4-yn-3-ol formed with thionyl chloride (in the presence of catalytic amount of DMF) to give 1-chloro-6,6-dimethylhept-2-en-4-yne (the ratio of Z and E isomers not specified).

Scheme 3 gives the formulas. This invention is not related to the preparation of terbinafine. It uses the chloro compound for other purposes.

SCHEME 3

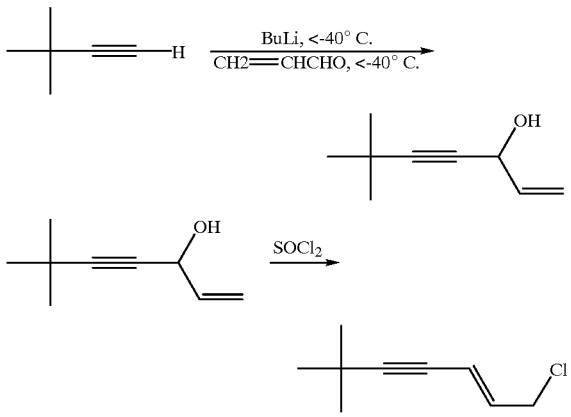

DETAILED DESCRIPTION OF THE INVENTION

As seen from the prior art the preparation of 6,6-dimethylhept-1-en-4-yn-3-ol, which is the key intermediate required for the manufacturing of terbinafine has two characteristics. First, it uses butyllithium for the generation of the t-butylacetylide required for the condensation with acrolein. Second, the condensation is carried out at low temperatures (−75° C. according to one source and −40° C. or less according to another).

Although both requirements can be met in industrial scale production, they cannot be considered as desired ones. Butyllithium is commercially available in large quantities but it is a highly dangerous substance. It is usually manufactured as 15% solution in hexane. However this is a pyrophoric material which ignites spontaneously in air (and the presence of hexane makes the situation even worse), and extremely sensitive to air and moisture. The handling of butyllithium is therefore a difficult and dangerous task. The transportation of this material is also problematic due to strict regulations.

The temperatures cited in the literature for the condensation of t-butylacetylide and acrolein are well below the so-called ordinary temperature range in the chemical industry. Temperatures of 0° C. to −15° C. can be regularly achieved in the chemical industry using conventional technology. Operating at −40° C. or below is possible and the technologies are available. However, special equipment must be constructed, and the current operation is tedious and costly.

Attempts to replace the undesired butyllithium with other reagents in order to generate the t-butylacetylide proved to be a non-trivial issue. We have tried several organometallic compounds and other appropriate agents but found out that these reagents cause rapid polymerization of acrolein. Hardly, if any of the desired product 6,6-dimethylhept-1-en-4-yn-3-ol was formed. Thus, the use of sodamide, lithium diisopropylamide, sodium hydride and calcium hydride was futile. Polymers of acrolein were formed instead. Surprisingly we had found that the reaction between t-butylacetylide and acrolein can be conducted with an acetylide made of t-butylacetylene and an organomagnesium compound of the Grignard type having the formula RMgX wherein R is an alkyl or aryl group and X is a halogen atom chosen from the list of chlorine, bromine and iodine. Especially preferred organomagnesium compound is ethylmagnesium bromide.

Ethylmagnesium bromide prepared in ether or toluene-tetrahydrofuran mixture is reacted with t-butylacetylene. Ethane is evolved and t-butylacetylide is formed. The reaction is carried out at slightly elevated temperature (up to 40° C.) for several hours. The next step was described to take place at low temperatures (at −40° C. or below or at −75° C. To any chemist who is skilled in the art these low temperatures seem to be the correct conditions. On one hand such reactions are usually carried out at such conditions, and on the other hand the aim of lowering the temperature is required in order to avoid polymerization of acrolein. This chemical substance is notorious for its tendency to polymerize under almost any conditions. Commercial acrolein is usually supplied containing a small amount of hydroquinone in it in order to reduce this tendency. It was not surprising that scientists of two large chemical companies (Sandoz as documented in EP24,587 and Sumitomo in EP341,048) chose to work at very low temperatures. To our complete astonishment. we have found out that the reaction between the acetylide formed in the reaction of t-butylacetylene and Grignard reagents, preferably with ethylmagnesium bromide, and acrolein can be equally well done at temperature range of −40° C. to +20° C. preferably at 0° C.–5° C. without significant amount of acrolein polymerization. This leads to a high yield of the desired product -6,6-dimethylhept-1-en-4-yn-3-ol.

The significance of this invention is comprised of two facts. First, it enables one to produce 6,6-dimethylhept-1-en-4-yn-3-ol avoiding the use of the hazardous and difficult to handle butyllithium. Second, this process can be carried out using regular equipment without the need for special, expensive to build and difficult to use dedicated production systems.

Having the above results we had repeated the procedure outlined in EP24,587 but adding the acrolein at about 0° C. instead of −75° C. according to the literature source. To our amazement we found that the reaction between lithium t-butylacetylide and acrolein proceeds well even at the relatively high temperature we used. While literature reported yield of 64% for 6,6-dimethylhept-1-en-4-yn-3-ol we found our procedure to give a similar yield of 60.5% (distilled material). The technological advantage of working at ∼0° C. should be emphasized again.

We have also tried to conduct the reaction using metallic lithium to generate the acetylide. It was found that although the reaction of lithium with t-butylacetylene is slow, it can be conducted successfully at temperature range of 20°–60° C. The next step (reaction with acrolein) was conducted at ∼0° C. and proceeded smoothly.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments

EXAMPLE 1

At dry and inert atmosphere, magnesium (6.4 gr., 0.26 mole) was heated with a trace of iodine until brown vapors evolved (~60° C). It was cooled down to room temperature and toluene (300 ml) and tetrahydrofuran (30 ml) were added. The mixture was heated to 45°–50° C. and a mixture of ethyl bromide (30 gr., 0.26 mole) and toluene (30 ml) was added dropwise. The mixture was stirred at 50° C. until all the magnesium had practically been consumed. The mixture was cooled and a mixture of t-butylacetylene (20 gr., 0.24 mole) mixed with toluene (20 ml) was added gradually. The mixture was stirred at 30°–40° C. for 4–6 hours. Progress of the reaction could be monitored by the evolution of ethane. The reaction mixture was cooled to 0° C.–5° C. and a mixture of acrolein (stabilized by hydroquinone) (14 gr., 0.25 mole) diluted with toluene (20 ml) was added gradually during 1 hour. The mixture was heated to room temperature and stirred for 4 hours. The reaction mixture was quenched with ammonium chloride solution. The phases were separated. The organic phase was extracted with toluene (3×50 ml). The combined organic phases were washed with water to neutrality. The solution was dried and the solvent stripped. The crude product was obtained (20.2 gr., 65% yield). The crude product was distilled (boiling point 68° C.–69.5° C. at 12 mbar) to give pure 6,6-dimethylhept-1-en-4-yn-3-ol (16.1 gr., 48%).

EXAMPLE 2

The procedure outlined in example 1 was repeated using n-propyl bromide instead of ethyl bromide. 6,6-dimethylhept-1-en-4-yn-3-ol (14.9 gr.) of similar purity was obtained.

EXAMPLE 3

Butyllithium 1.6 M solution in hexane (106.2 ml, 0.17 mole) was added dropwise during 70 minutes to a mixture of t-butylacetylene (13.3 gr., 0.162 mole) and tetrahydrofuran (133.1 ml) at 0° C. A solution of freshly distilled acrolein (10 gr., 0.17 mole) in tetrahydrofuran (26.6 ml) was added to the reaction mixture at 0° C. during 45 minutes. The reaction mixture was stirred at 0° C. for 40 minutes. It was further stirred for 18 hours at room temperature. Saturated ammonium chloride solution (45 ml) was added. The reaction mixture was brought to pH 6 using 10% sulfuric acid (about 85 ml). Tetrahydrofuran was evaporated under reduced pressure. The residue was extracted by dichloromethane. The organic phase was washed with water and dried. The dichloromehane was removed to give the crude product (20.1 gr., 90% yield). Pure 6,6-dimethylhept-1-en-4-yn-3-ol was obtained by distillation. Boiling point was 83° C. at 24 mbar. 13.5 gr. were obtained (60.6% yield).

EXAMPLE 4

Under a blanket of dry nitrogen, at 0° C., metallic lithium (0.667 gr., 0.096 mole) was added to a mixture of t-butylacetylene (9.94 gr., 0.121 mole) and tetrahydrofuran (75 ml). The mixture was heated to 40° C. for 5 hours and kept at room temperature for 24 hours. The lithium was almost completely consumed. A second amount of t-butylacetylene (9.94 gr., 0.121 mole) was added and the reaction mixture was stirred for 21 hours. The mixture was cooled to 0° C. and a solution of freshly distilled acrolein (6.634 gr., 0.118 mole) in tetrahydrofuran (10 ml) was added gradually during 30 minutes. The mixture was stirred at 0° C. for 30 minutes and then at room temperature for 3 hours. Isopropanol (6 ml) was added to quench the remaining lithium. The mixture was quenched using saturated ammonium chloride aqueous solution (30 ml) at 0° C. The pH was brought to 6 by 10% sulfuric acid (ca. 45 ml). The tetrahydrofuran and excess t-butylacetylene were evaporated and the mixture was extracted 3 times by dichloromethane (70 ml each time). The organic phase was washed with water (2×20 ml), dried and the solvent evaporated to give 10.2 gr. of an almost pure 6,6-dimethylhept-1-en-4-yn-3-ol (73.9% yield).

EXAMPLE 5

A mixture of t-butylacetylene (6.9 gr., 0.084 mole) and tetrahydrofuran (15 ml) was added during 90 minutes to a 1 M solution of phenylmagnesium bromide in tetrahydrofuran (80 ml, 0.08 mole) at 40° C. under nitrogen blanket. The reaction mixture was stirred for 3 hours at 40° C. and left overnight at room temperature. After cooling to 0° C. freshly distilled acrolein (4.54 gr., 0.081 mole) mixed with tetrahydrofuran (6 ml) was added during 1 hour. Stirring was continued for 4 more hours at room temperature. The mixture was cooled to 0° C. and saturated solution of ammonium chloride in water (30 ml) was added slowly. Then the pH was corrected to 6 using 10% sulfuric acid (42 ml). The organic volatile materials were evaporated. The residue was extracted with dichloromethane (3×70 ml). The organic phase was washed with water (100 ml), dried and the solvent evaporated. GC analysis of the mixture showed the presence of 6,6-dimethylhept-1-en-4-yn-3-ol and 3-phenyl-3-hydroxypropene in similar amounts. The latter product was formed by 1,2 addition of phenylmagnesium bromide to acrolein.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the preparation of 6,6-dimethylhept-1-en-4-yn-3-ol comprising:
   (i) reacting t-butylacetylene with a proton-extracting agent selected from the group consisting of an organometallic compound and metallic lithium to form a t-butylacetylide, wherein said organometallic compound has the formula $R_2Li$ where $R_2$ is an alkyl or aryl group;
   (ii) reacting said acetylide with acrolein at temperatures between −40° C. to ±20° C.;
   (iii) quenching the reaction mixture; and
   (iv) isolating the product.
2. A process as claimed in claim 1, wherein said organometallic compound is butyllithium.
3. A process as claimed in claim 1, wherein acrolein is added at a temperature range of −20° C. to +10° C.
4. A process as claimed in claim 1, wherein acrolein is added at a temperature range of 0° C. to +5° C.

* * * * *

UNITED STATES PATENT AND TRADEMARK OFFICE
CERTIFICATE OF CORRECTION

PATENT NO.     : 6,570,044 B2
DATED          : May 27, 2003
INVENTOR(S)    : Joseph Kaspi et al.

It is certified that error appears in the above-identified patent and that said Letters Patent is hereby corrected as shown below:

Column 6,
Line 57, "±20º C." has been replaced with -- +20º C. --.

Signed and Sealed this

Seventh Day of October, 2003

JAMES E. ROGAN
*Director of the United States Patent and Trademark Office*